(12) United States Patent
Ishihara et al.

(10) Patent No.: US 7,148,007 B2
(45) Date of Patent: Dec. 12, 2006

(54) METHOD FOR EVALUATING IMMUNOTOXICITY OF TEST SUBSTANCE

(75) Inventors: Mitusuko Ishihara, Tokyo (JP); Satoshi Itoh, Niihari-gun (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 707 days.

(21) Appl. No.: 10/200,164

(22) Filed: Jul. 23, 2002

(65) Prior Publication Data
US 2003/0040025 A1 Feb. 27, 2003

(30) Foreign Application Priority Data

Jul. 24, 2001 (JP) ............................. 2001-223160
Sep. 20, 2001 (JP) ............................. 2001-287152

(51) Int. Cl.
*C12Q 1/02* (2006.01)
*C12Q 1/18* (2006.01)
*C12Q 1/32* (2006.01)
*C12Q 1/68* (2006.01)

(52) U.S. Cl. .............................. 435/6; 435/26; 435/29; 435/32

(58) Field of Classification Search .................. 435/29, 435/32, 6, 26; 703/11, 12; 706/18, 21
See application file for complete search history.

(56) References Cited

U.S. PATENT DOCUMENTS 5,801,193 A * 9/1998 Ojo-Amaize et al. ....... 514/475
6,265,180 B1 * 7/2001 Zuelli et al. ................... 435/29
6,587,845 B1 * 7/2003 Braunheim .................... 706/21
6,723,527 B1 * 4/2004 Pettit et al. .................... 435/29
6,969,729 B1 * 11/2005 Jensen et al. ................ 514/418
2003/0040025 A1 * 2/2003 Ishihara et al. ............. 435/7.21

FOREIGN PATENT DOCUMENTS

EP          0953632       *   2/1999

OTHER PUBLICATIONS

Kacani et al, Folia Biologica (Praha), 42, 11-16, 1996.*
C. W. Johnson, et al. "Sensitivity of the SRBC PFC Assay Versus Elisa for Detection of Immunosuppression by TCDD and TCDD-Like Congeners" Toxicology, 2000, pp. 1-11.

(Continued)

*Primary Examiner*—David Saunders
(74) *Attorney, Agent, or Firm*—Oblon, Spivak, McClelland, Maier & Neustadt, P.C.

(57) ABSTRACT

The present invention discloses a method of evaluating the immunotoxicity of a hydrophobic test substance, comprising (1) culturing immunocompetent cells in a culture system containing a hydrophobic test substance and a surfactant, (2) obtaining a survival rate of the immunocompetent cells after the culturing (1), and (3) evaluating the immunotoxicity of the hydrophobic test substance from the survival rate obtained in (2).

4 Claims, 6 Drawing Sheets

OTHER PUBLICATIONS

Beths A. Vorderstrasse, et al. "2,3,7,8-Tetrachlorodibenzo-P-Dioxin Affects the Number and Function of Murine Splenic Dendritic Cells and Their Expression of Accessory Molecules" Toxicology and Applied Pharmacology, 2001, pp. 117-125.

Satoshi Itoh, et al. "Relationship Between Toxicity and Electronic Strucutres of Dioxins: DFT and Neural-Network Approaches" AIChE Symposium Series vol. 97, 2001, pp. 180-182.

U.S. Appl. No. 11/174,660, filed Jul. 6, 2005, Itoh.

Toshihiro Fujii, et al., "Quantitative Risk (Toxicity) Evaluation System for Dioxin, Session of Research Report on Research and Development for Applying Advanced Computational Science and Technology-Progressive Third Science", Japan Science and Technology Agency, H10 (1998) Short Term Type, Dec. 31, 2000, pp. 96-97.

Shinichi Kikuchi, et al., "Discovery of Rules and Improvement of Generalization Power using SFNN and Destructive Structural Learning Algorithm", Technical Research Report of the Institute of Electronics, Information and Communication Engineers, vol. 98, No. 219, Jul. 27, 1998, pp. 31-38, (with English Abstract).

Ikuo Moriguchi, "Development of Quantitative Structure-Activity Relationships and Computer-Aided Drug Design", Pharmaceutical Society of Japan, vol. 114, No. 3, Mar. 25, 1994, pp. 135-146.

* cited by examiner

| Input parameter | Output parameter | |
|---|---|---|
| Index for specifying chemical substance | Numerical value correlated to charge on each atom | Inner parameter of nonlinear model |
| A A A B B B ⋮ | X X X P P ⋮ | Y Y Q Q ⋮ |

METHOD FOR EVALUATING IMMUNOTOXICITY OF TEST SUBSTANCE

CROSS-REFERENCE TO RELATED APPLICATIONS

This application is based upon and claims the benefit of priority from the prior Japanese Patent Applications No. 2001-223160, filed Jul. 24, 2001; and No. 2001-287152, filed Sep. 20, 2001, the entire contents of both of which are incorporated herein by reference.

BACKGROUND OF THE INVENTION

1. Field of the Invention

The present invention relates to an in-vitro method for evaluating the immunotoxicity of a test substance.

2. Description of the Related Art

Recently, the toxicity of exogenous endocrine disrupting substances such as dioxins has become a social problem. In general, the exogenous endocrine disrupting substances are also called environmental hormones. The toxicity of such environmental hormones cause a wide variety of disorders including reproductive disorders, immunological disorders, and CNS (central nervous system) disorders.

For example, it has been reported that heavy exposure to dioxins causes convulsive contraction of thymus glands in C57B1/1 mice, (Kerkvliet N. I. et al. Environmental Research 52, pp146–154 (1990)). As is described in this report, acute immunotoxicity tests for chemical substances are usually carried out in-vivo by using animals. However, such in-vivo testing is not suitable for use in screening numerous test substances quickly.

On the other hand, to detect the environmental hormonal toxicity of various substances including novel substances, the following conventional in-vitro tests are used including an E-SCREEN method, which specifically detects the estrogen action of an environmental hormone (Soto A. et al. Environ. Health Perspect, 103, pp113–122 (1995)) and a two-hybrid assay (Nishihara J. et al., Toxcol. Appl. Pharmacol. 154, pp76–83 (1999)).

In these conventional methods, the estrogen action and androgen action are detected to find reproductive toxicity.

As an in-vitro assay system for detecting immunotoxicity, an evaluation method using a human T cell line is known (A. Hossain et al. (1998), J. Biol. Chem. 273 (31), pp19853–19858). However, this method uses apoptosis as a reference and merely detects extremely limited cytotoxicity.

As described above, an in-vitro assay system for detecting the toxicity of endocrine disrupting substances other than the reproductive toxicity has not yet been established at present.

BRIEF SUMMARY OF THE INVENTION

In view of the aforementioned problems, the present invention provides a method for detecting the toxicity of a test substance, particularly, an endocrine disrupting activity of the test substance, more particularly, toxicity except toxicity on the reproductive system.

According to a first aspect of the present invention, there is provided a method of evaluating the immunotoxicity of a hydrophobic test substance, comprising:

(1) culturing immunocompetent cells in a culture system containing a hydrophobic test substance and a surfactant;

(2) obtaining a survival rate of the immunocompetent cells after the culturing (1); and (3) evaluating the immunotoxicity of the hydrophobic test substance from the survival rate obtained in (2).

According to a second aspect of the present invention, there is provided a method of evaluating the immunotoxicity of a hydrophobic test substance, comprising:

(1) culturing immunocompetent cells in a first culture system containing a hydrophobic test substance and a surfactant and simultaneously in a second culture system containing a surfactant alone;

(2) obtaining a survival rate of the immunocompetent cells in each of the first and second culture systems after the culturing (1); and (3) comparing the survival rates of cells of the first and second culture systems obtained in (2) to each other, evaluating the immunotoxicity of the hydrophobic test substance.

According to a third aspect of the present invention, there is provided a method of evaluating the immunotoxicity of a hydrophobic test substance comprising:

(1) culturing immunocompetent cells in a first culture system containing a hydrophobic test substance and a surfactant and simultaneously in a second culture system containing the surfactant without the hydrophobic test substance;

(2) obtaining a survival rate of the immunocompetent cells in each of the first and second culture systems after the culturing (1); and (3) comparing the survival rates of cells of the first and second culture systems obtained in (2) each other, evaluating the immunotoxicity of the hydrophobic test substance.

By the methods mentioned above, an in-vitro assay system for detecting the toxicity of a chemical substance is provided.

According to a fourth aspect of the present invention, there is provided a method of evaluating the immunotoxicity of a second chemical substance, comprising:

(1) obtaining intramolecular charge distribution of a first chemical substance and charges of atoms located at predetermined positions of a molecule thereof based on geometric data concerning a molecular structure and physical characteristics of constitutional atoms thereof;

(2) performing the method of evaluating the immunotoxicity of a hydrophobic test substance according to the first aspect by using the first chemical substance as the hydrophobic test substance, thereby obtaining a toxicity value, which indicates the degree of toxicity of the first chemical substance;

(3) obtaining intramolecular charge distribution of a second chemical substance and charges of atoms located at predetermined positions of a molecule thereof based on geometric data concerning a molecular structure and physical characteristics of constitutional atoms thereof; and (4) predicting the immunotoxicity of the second chemical substance from the intramolecular charge distribution and charge of the second chemical substance obtained in (3) based on the correlation between the intramolecular charge distribution, charge, and molecular structure of the first chemical substance obtained in (1) and the toxicity value obtained in (2), thereby evaluating the immunotoxicity of the second chemical substance.

According to a fifth aspect of the present invention, there is provided a program signal for executing a method of evaluating the immunotoxicity of a second chemical substance; comprising:

(1) performing the method of evaluating the immunotoxicity of a hydrophobic test substance according to the first aspect by a user by using a first chemical substance as the hydrophobic test substance, thereby obtaining a toxicity value, which indicates the degree of toxicity of the first chemical substance;

(2) inputting geometric data concerning molecular structures of the first chemical substance and a second chemical substance and data on physical characteristics of constitutional atoms thereof and inputting the toxicity value of the first chemical substance obtained in (1) by the user into a data input section through input means;

(3) calculating intramolecular charge distribution each of the first and second chemical substances in accordance with the procedure previously stored in memory means and based on the data input in (2) in an electronic structure analysis section, thereby obtaining charges of atoms located at predetermined positions;

(4) obtaining a function indicating the correlation between the intramolecular charge distribution and charge of the first chemical substance molecule obtained in (3) in accordance with the procedure previously stored in memory means by a chemo-metric analysis section; and (5) converting the intramolecular charge distribution and the amount of charge of the second chemical substance molecule obtained in (3) by using the function obtained in (4) in a toxicity evaluation section to obtain a toxicity value of the second chemical substance, thereby evaluating the immunotoxicity of the second chemical substance.

According to a sixth aspect of the present invention, there is provided a method of evaluating the immunotoxicity of a second chemical substance, comprising:

(1) obtaining intramolecular charge distribution of a first chemical substance and charges of atoms located at predetermined positions of a molecule thereof based on geometric data concerning a molecular structure and physical characteristics of constitutional atoms thereof;

(2) performing the method of evaluating the immunotoxicity of a hydrophobic test substance according to the first aspect by using the first chemical substance as the hydrophobic test substance, thereby obtaining a toxicity value, which indicates the degree of toxicity of the first chemical substance;

(3) obtaining intramolecular charge distribution of a second chemical substance and charges of atoms located at predetermined positions of a molecule thereof based on geometric data concerning a molecular structure and physical characteristics of constitutional atoms thereof;

(4) predicting the immunotoxicity of the second chemical substance from the intramolecular charge distribution and charge of the second chemical substance obtained in (3) based on the correlation between the intramolecular charge distribution, charge, and molecular structure of the first chemical substance obtained in (1) and the toxicity value obtained in (2), thereby evaluating the immunotoxicity of the second chemical substance.

According to a seventh aspect of the present invention, there is provided a method of evaluating the toxicity of a second chemical substance, comprising:

(1) performing the method of evaluating the immunotoxicity of a hydrophobic test substance according to the first aspect by a user by using a first chemical substance as the hydrophobic test substance, thereby obtaining a toxicity value, which indicates the immunotoxicity of the first chemical substance;

(2) inputting geometric data concerning molecular structures of the first chemical substance and the second chemical substance and data on physical characteristics of constitutional atoms thereof, and inputting the toxicity value of the first chemical substance obtained in (1) into a data input section through input means by the user;

(3) calculating the intramolecular charge distribution of each of the first chemical substance and the second chemical substance in an electronic structure analysis section in accordance with the procedure previously stored in memory means based on the geometric data concerning molecular structures of the first chemical substance and the second chemical substance and data on physical characteristics of constitutional atoms thereof input in (2), thereby obtaining charges of atoms located at predetermined positions;

(4) obtaining a function indicating the correlation between the intramolecular charge distribution and charge of the first chemical substance calculated in (3) and the toxicity value obtained in (1) in accordance with the procedure previously stored in memory means by a chemo-metric analysis section; and (5) converting the intramolecular charge distribution and charge of the second chemical substance obtained in (3) by using the function obtained in (4) to obtain a toxicity value of the second chemical substance, thereby evaluating the immunotoxicity of the second chemical substance.

As described above, a method for detecting the toxicity of a chemical substance is provided.

DETAILED DESCRIPTION OF THE INVENTION

1. Explanation of Terms

The term "endocrine disrupting substance" to be detected by the embodiment of the present invention refers to an exogenous chemical substance which inhibits various processes, such as synthesis, storage, secretion, transportation, receptor-binding, action-initiating, and excretion processes of endogenous hormones responsible for homeostasis, reproduction, development, and behavior of living creatures. The endocrine disrupting substance is generally called an exogenous endocrine disrupting substance, endocrine disrupting substance, endocrine brockading substance or environmental hormone. Generally, such an endocrine disrupting substance, even if it is present in an extremely small amount from ppb to ppt, has a chronic effect upon various systems including the reproduction system, nervous system and immune system.

2. Method for Evaluating Immunotoxicity of Test Substance

As described above, an endocrine disrupting substance has a chronic effect upon living creatures at an extremely low concentration. Therefore, it is difficult for a conventional method to evaluate the immunotoxicity of an endocrine disrupting substance in a short time. In addition, the immunotoxicity detected by the conventional method is limited. In another case where an endocrine disrupting substance having a lower toxicity than a generally known endocrine disrupting substance is tested, not only a much longer time is required for the detection but also there is a high possibility to overlook the toxicity. Hence, it is difficult to detect the immunotoxicity of such an endocrine disrupting substance by such a conventional method.

Surprisingly, according to an embodiment of the present invention, there is provided an in-vitro assay for detecting the immunotoxicity of an endocrine disrupting substance. Furthermore, according to an embodiment of the present invention, it is possible to detect the immunotoxicity of an endocrine disrupting substance quickly and accurately by a simple procedure.

According to an embodiment of the present invention, there is provided a method of evaluating the immunotoxicity of a test substance by culturing immunocompetent cells under the presence of the test substance and a surfactant to obtain the viability (survival rate) of the immunocompetent cells.

3. First Embodiment

Figure 1:
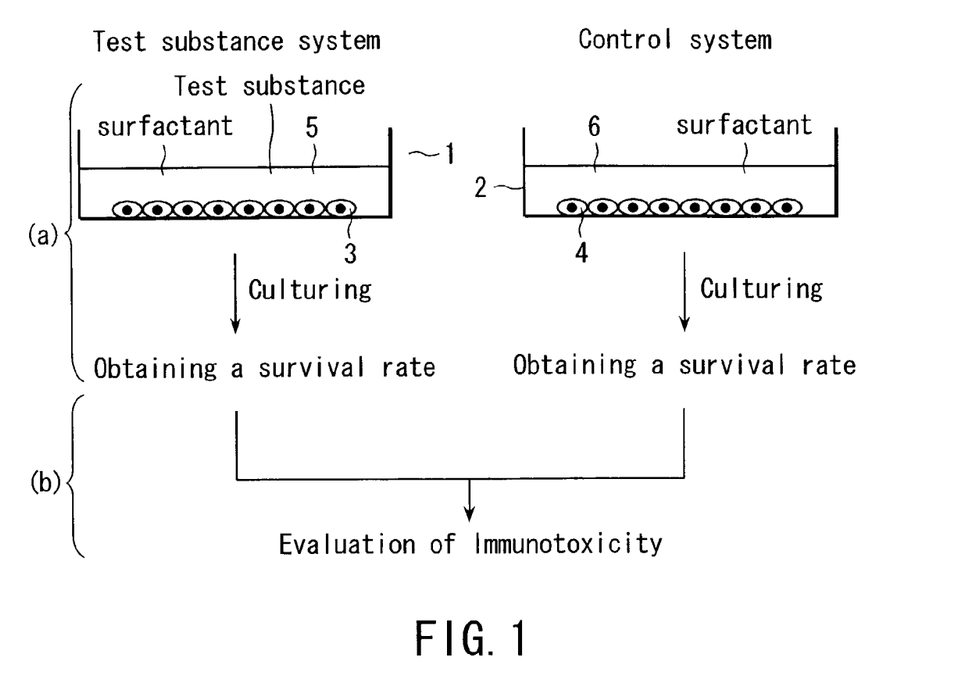
FIG. 1 is an illustration showing a method according to an embodiment of the present invention.

Now, a first embodiment of the present invention will be explained with reference to FIG. 1.

The method of evaluating the immunotoxicity of a test substance according to an embodiment of the present invention is performed by carrying out the following steps (a) and (b), successively.

(a) In-vitro Assay System of Exogenous Endocrine Disrupting Substance

Immunocompetent cells are cultured in two culture systems. In a culture system 1, immunocompetent cells 3 are cultured in a medium 5 containing a test substance and a surfactant. In culture system 2, the immunocompetent cells 4 are cultured in a medium 6 containing the surfactant alone. More specifically, the culture system 1 is a test-substance system for exposing immunocompetent cells to a test substance, whereas the culture system 2 is a control system for culturing the immunocompetent cells in the absence of the test substance.

(b) Immunotoxicity Evaluation of Exogenous Endocrine Disrupting Substance

The viability is obtained with respect to cells in two culture systems obtained in the step (a).

By comparing the viabilities, the immuno-toxicity of a test substance is evaluated.

Examples of the immunocompetent cells to be used in the present invention may include cells isolated from the immune tissue such as the spleen, the thymus gland, or the marrow purified lymphocytes, any one of established cells, cancerous cells and tumor cells, and any one of cells obtained by modifying these cells by a known cell-engineering method. Typically, dendritic cells and established cells, such as JAWS II, may be used but not limited to these.

Furthermore, cells improved in dioxin receptivity by some means may be used. As an example of such cells, dendritic cells are reported which have allylhydrocarbon receptors capable of binding to a dioxin and improved in expression level (Vorderstrasse B. A et al. Toxcol. Appl. Pharmacl. 171, pp117–125 (2001)). The document shows significant increase of the receptivity of dendritic cells to a dioxin. Such dendritic cells may be used in accordance with the present invention. The content of this document is incorporated herein by reference.

It is desirable that the surfactant to be used in the present invention have a low protein denaturation function and a low critical micelle concentration (hereinafter referred to as "cmc"). Examples of the surfactant include anionic surfactants having a steroid ring, namely, cholic acid based surfactants such as a sodium deoxycholic acid; nonionic surfactants having a polyoxylene chain, namely, polyoxyethylene based surfactants such as polyoxyethylene (23) lauryl ether. Polyoxyetehylene (23) lauryl ether is purchased from Wako Pure Chemical Industries Ltd. and Sigma (Chemical) Co. or from ICI Co., Ltd., under a trade name of Brij35, however not limited to these.

The concentration of a surfactant varies depending upon the type of the surfactant to be used. For example, when polyoxyethylene (23) lauryl ether is used as a surfactant, the content of the surfactant may be about 30 $\mu$M or less, desirably about 10 to 30 $\mu$M. When polyoxyethylene (20) cetyl ether is used as a surfactant, the content of the surfactant may be 5 $\mu$M or less.

Any medium may be used in the present invention as long as it is a conventional medium known to those skilled in the art and suitable for the immunocompetent cells to be used. Culturing may be performed for a sufficient time to observe difference in viability (survival rate). As to other culturing conditions including temperature and $CO_2$ concentration, any conditions may be used as long as they are conventionally used, suitable for the cells to be used, and known to those skilled in the art.

The viability of the cells may be determined by using a conventionally known method for counting the number of living cells, for example, a viability measurement method such as an oxidation-reduction method such as the MTT method or the LDH method, $^3$H-thymidine take-up method, or the trypan blue exclusion test. In addition, any method or a modified method thereof may be used as long as it can measure the number of living cells. Alternatively, the number of living cells may be measured based on the difference in doubling time and difference in light transmissibility due to cell density. In this manner, immunotoxicity can be evaluated based on the number of living cells.

Alternatively, the viabilities obtained in the test-substance system and the control system are statistically compared with each other to obtain the presence or absence of a significant difference. Based on the significant difference, the immunotoxicity may be evaluated.

In the aforementioned embodiment, the immunotoxicity is evaluated by comparing the viabilities of two culture systems. However, another method mentioned below may also be used. Immunocompetent cells are cultured only in a medium containing a test substance and a surfactant to obtain a growth curve, and then, the immunotoxicity is evaluated based on the growth curve or by comparing the growth curve with a threshold value arbitrarily selected in advance.

According to the embodiment of the present invention, the effect of an endocrine disrupting substance upon the immune system can be detected by determining the lethal effect of the endocrine disrupting substance upon the immunocompetent cells.

According to the embodiment of the present invention, there is provided a cell culture system capable of determining the lethal effect of an endocrine disrupting substance upon the immunocompetent cells. Basically, such a cell culture system has a medium containing a test substance and a surfactant and used for culturing immunocompetent cells.

According to the embodiment of the present invention, it is possible to detect the immunotoxicity of an endocrine disrupting substance in a similar manner to in detecting the acute immunotoxicity.

According to this embodiment of the present invention, it is possible to detect the immunotoxicity of substances such as endocrine disrupting substances, chemical substances, novel substances, waste substances, and naturally-occurring substances, easily and more precisely, even if the toxicity of a substance extremely low.

4. Second Embodiment

According to a further aspect of the present invention, it is possible to predict (evaluate) the toxicity of a substance of unknown toxicity by virtual screening, which is performed by using experimental data obtained in accordance with the method of the first embodiment.

Figure 2:
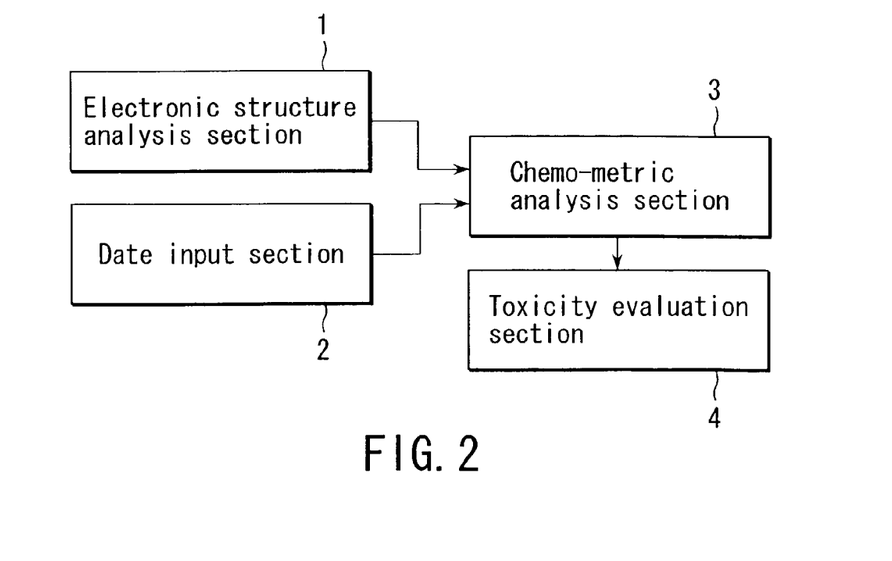
FIG. 2 is a schematic block diagram showing a chemical substance toxicity evaluation device for use in an embodiment of the present invention.

FIG. 2 shows a chemical substance toxicity evaluation apparatus for evaluating (predicting) the toxicity of a substance. FIG. 2 is a block diagram showing a schematic functional structure of the chemical substance toxicity evaluation apparatus according to the present invention. The chemical substance toxicity evaluation apparatus according to this embodiment comprises an electronic structure analysis section 1, a data input section 2, a chemo-metric analysis section 3 and a toxicity evaluating section 4 (see FIG. 2). The electronic structure analysis section 1 and data input section 2 are connected to the chemo-metric analysis section 3, which further connected to the toxicity evaluation section 4 (see FIG. 2). However, if necessary, all sections are connected to each other.

According to the embodiment of the present invention, the chemical substance toxicity evaluation apparatus may comprise at least one of input means such as a key board or mouse for inputting data by the operator (user), at least one of memory means such as a memory for storing various data items, at least one of processing means such as a CPU for performing various processing operations in accordance with the program previously stored in the memory means or the data input by the input means, and at least one of output means such as a display or printer for outputting data such as the results processed by the processing means and input data.

The electronic structure analysis section 1, and data input section 2, the chemo-metric analysis section 3 and the toxicity evaluation section 4 may be operated under the control of a single processing means in accordance with the program stored in a single memory means or the data input by a single input means, with the result that a predetermine function or effect may be obtained, in short, desired data may be output. Alternatively, each of the sections 1, 2, 3, 4 may have a single input means, processing means, memory means and output means. These means may be connected to each other to mutually transmit data. Some of the sections have a common input means, processing means, memory means and/or output means. These means may be connected to each other to mutually transmit data.

Now, the function of the chemical substance toxicity evaluation apparatus according to the embodiment of the present invention comprising a single input means, memory means, processing means, and output means will be explained. To be more specific, processing is performed in each of the electronic structure analysis section 1, data input section 2, chemo-metric analysis section 3 and toxicity evaluation section 4 under the control of the single processing means in accordance with the program stored in a single memory means or data input from the input means. However, the present invention is not limited to such a structure and may be modified in accordance with the structure of the chemical substance toxicity evaluation apparatus as long as the technical idea of the present invention can be attained.

The chemical substance toxicity evaluation apparatus according to the embodiment of the present invention has four sections (as shown in FIG. 2), namely, the electronic structure analysis section 1, data input section 2, chemo-metric analysis section 3, and toxicity evaluation section 4.

The operator inputs data such as geometric data on the molecular structure of the chemical substance to be evaluated and the physical characteristic data (mass, atomic number) of constituent atoms by means of an input means. In the electronic structure analysis section 1, the processing means calculates the charges of individual atoms located at predetermined positions of a molecule in accordance with a predetermined procedure (e.g. the procedure shown in FIG. 3) previously stored in the memory section and based on the input data. On the other hand, the processing means calculates the charges to be assigned to predetermined atoms, which are specified by the operator through the input means. After the amount of charge is calculated, the processing means transfers the calculation results, i.e, amount of charge, from the electronic structure analysis section 1 to the chemo-metric analysis section 3. At this time, the processing means may output the data on the amount of charge to the operator through the output means.

The data input section 2 consists of an input means from which the operator inputs data therefrom. Various data items may be input from the data input section 2, as needed. Alternatively, the data input section 2 may include an input means, a processing means, and a memory means. In this case, the operator performs the following steps.

The operator inputs experimental data on the toxicity of a chemical compound through the input means.

Based on the experimental data and data stored in the memory means, the processing means converts the toxicity of the chemical compound into a numerical value to obtain a toxicity index. The conversion into the toxicity index may be performed by the processing means. The converted data is stored in the memory means. If necessary, the processing means may call data from the memory means and transfer it to a desired section. Alternatively, the operator may convert the toxicity of a chemical compound into a numerical value based on the data such as experimental data and data base regarding the toxicity of the chemical compound in advance, and thereafter, the resulting toxicity index may be input into the data input section as the data through the input means. In the data input section, the processing means may transfer the toxicity index thus input to the memory means and stored therein. If necessary, the processing means calls data from the memory means and transfers it to a desired section.

The toxicity converted into a numerical value from raw data is referred to as "toxicity index". The toxicity index is data collected from clinical data or experimental data. Any data may be used as the toxicity index as long as it shows the relationship between the molecular structure of a chemical compound and the toxicity index shown by the compound molecule.

The processing means transfers the toxicity index obtained or input in the manner mentioned above to the chemo-metric analysis section 3 of the processing means.

In the chemo-metric analysis section 3, the function to be used in the data conversion and initial parameter values are set.

The chemo-metric analysis section 3 receives data on the molecular structure, charge distribution in the molecule, and charges on atoms located in predetermined positions of the molecule. Furthermore, the chemo-metric analysis section 3 receives data on the compound and its toxicity index from the data input section 2.

Figure 4:
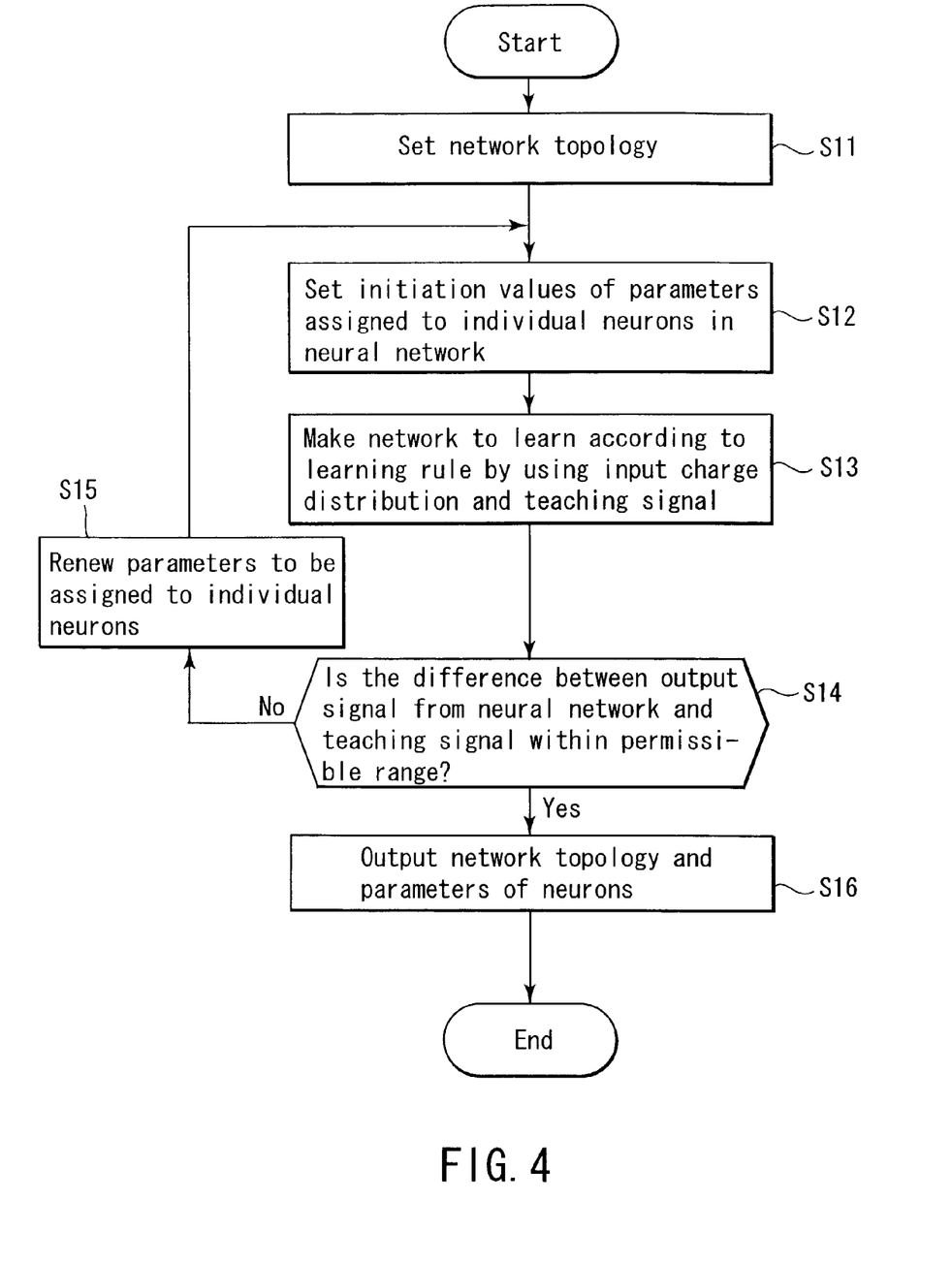
FIG. 4 is a flowchart showing the steps carried out in the chemo-metric analysis section installed in the chemical substance toxicity evaluation device shown in FIG. 2.

Based on the data, the following steps are performed in the chemo-metric analysis section 3 in accordance with the procedure shown in FIG. 4. First, the processing means sets a topology adequate for the function previously set and the initial parameter values. When a neural network is used as a chemo-metric analysis means, the topology for the network is input by the operator in the form of topology data from the data input section of FIG. 2. Thereafter, the parameters, e.g., weighting factor, of the neural network constituting the chemo-metric analysis section 3 is adjusted. The adjustment of parameters is called "learning" in the neural network. In the learning, the parameters are adjusted such that desirable output data (called "teaching signal") with respect to input data is obtained. To explain more specifically, as an input data, the amount of charge, which is transferred from the electronic structure analysis section 1, is input. Subsequently, the parameters are adjusted by the input data so as to obtain an appropriate toxicity index. The toxicity index determined based on experimental values is a teaching signal, which is also input by the operator through the data input section.

After completion of the learning, the processing means sends the data (i.e., network topology and weighting factors of individual neurons) constituting the neural network from the chemo-metric analysis section 3 to the toxicity evaluation section 4. After receiving the network topology of the neural network and the weighting factors of individual neurons from the chemo-metric analysis section 3, the processing means, in the toxicity evaluation section 4, reconstitutes the learned neural network based on these data. As a next step, in the toxicity evaluation section 4, the processing means receives the molecular data and the charges of the atoms located at predetermined positions of a molecule from the electronic structure analysis section 3. Further based on the molecular data and its toxicity index received from the data input section 2, the processing means transfers the charge of a molecule of a chemical substance of unknown toxicity (whose toxicity index has not yet been obtained) to a neural network as an input signal to be into the neural network. The neural network calculates based on the input signal and outputs the obtained value. The output value is an evaluation value exhibiting the toxicity of the chemical substance. The processing means may store the calculation result (value) in the memory means or may output it to the operator through the output means.

In the foregoing, the function of the chemical substance toxicity evaluation apparatus comprising a single input means, memory means, processing means, and output means according to the embodiment of the present invention has been explained. However, the present invention is not limited to these structure and may be modified in various ways in accordance with the structure of the chemical substance toxicity evaluation apparatus as long as the idea of the present invention can be attained. When the electronic structure analysis section 1 has an own input means, the operator may input the data into the electronic structure analysis section 1 through its own input means. Alternatively, in the electronic structure analysis section 1, the amount of charge may be calculated by the processing means exclusively provided to the electronic structure analysis section 1. More specifically, after a desired processing is performed by the means exclusively provided to each of the sections, data is transferred to a desired section where the next processing is to be performed.

Now, each section will be explained more specifically.

The data including the types and the number of atoms constituting a chemical substance and the presence and absence of chemical bonds between atoms with respect to a chemical substance (hereinafter, referred to as a "first chemical substance") having an experimentally-obtained toxicity and a chemical substance (hereinafter, referred to as a "second chemical substance") to be subjected to toxicity evaluation, is input into the electronic structure analysis section 1, as input data. After the data input, the electronic states of molecules are obtained by a predetermined numerical calculation method in accordance with fundamental physics or chemistry theoretical model. In this case, if the stable structure of the molecule is not experimentally obtained, the stable structure is obtained by calculating the force applied to each of atoms and moving the atoms in the direction of applying the force. The electronic states of the molecules constituting the stable structure are obtained. This method may be used even if the stable structure of a molecule is either known or not.

When the electronic states of molecules are calculated, the charge distribution in the molecules is obtained. In the electronic structure analysis section 1, charge is assigned to each atom. The results are supplied to the chemo-metric analysis section 3. The processing performed in the electronic structure analysis section 1 will be described later.

In the data input section 2, physicochemical data of a first chemical substance and experimental data on toxicity value of the first chemical substance are input.

In the chemo-metric analysis section 3, the charge distribution of some atoms is selected from the charge distributions of the atoms constituting the first chemical substance and supplied from the electronic structure analysis section 1. When the selected charge distribution is input, an inner parameter of a nonlinear model (e.g., neural network) is obtained such that the experimental data on a toxicity value input by the data input section 2 is output. The processing performed in the chemo-metric analysis section 3 will be described later.

In the toxicity evaluation section 4, the toxicity of a chemical substance of unknown toxicity (second chemical substance) is evaluated based on the nonlinear model having an inner parameter obtained in the chemo-metric analysis section 3. The processing performed in the toxicity evaluation section 4 will be described later.

Figure 3:
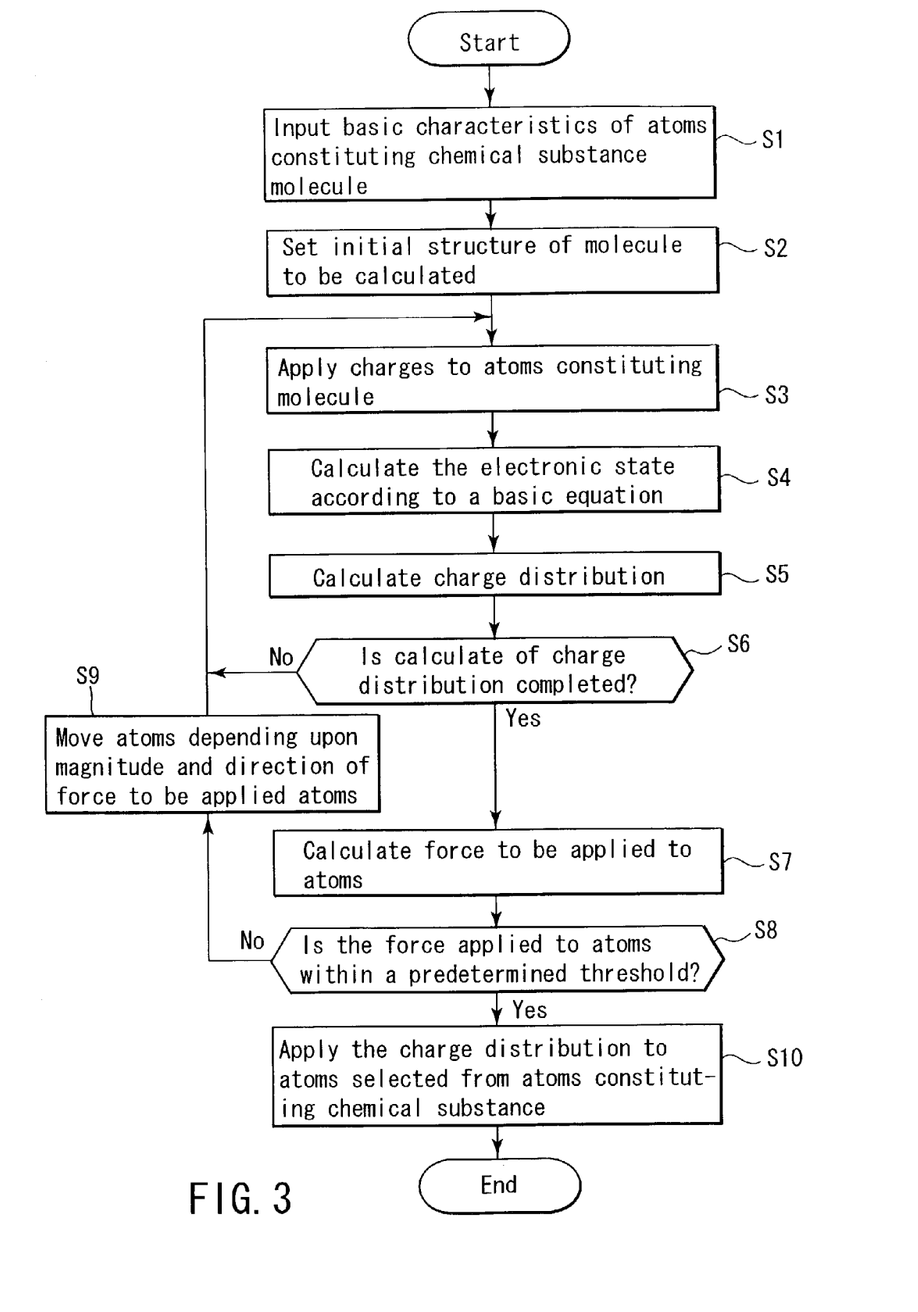
FIG. 3 is a flowchart showing the steps carried out in the electronic structure analyzing section installed in the chemical substance toxicity evaluation device shown in FIG. 2.

FIG. 3 is a flowchart showing the operation procedure performed in the electronic structure analysis section 1. First, the operator inputs fundamental characteristics (e.g., atomic mass, charge) of the atoms constituting a molecule of a chemical substance into the electronic structure analysis section 1 by an input means (Step 1).

In the present invention, it is desirable that both a first chemical substance having an experimentally-obtained toxicity value, and a second chemical substance to be evaluated for toxicity should belong to the same chemical compound group, which consists of chemical substances satisfying a specific rule.

Examples of such a chemical compound group consisting of chemical substances satisfying a specific rule are:

Isomers of a chemical substance such as structural isomers and stereo isomers, more specifically, geometrical isomers, rotational isomers and optical isomers; ionization isomers and ligand isomers having different ligands, linkage isomers different in intramolecular linkage between atoms;

Chemical compounds having different substituents;

Derivatives;

Adduct compounds;

Chemicals from which different leaving groups are removed,

Condensates; and chemicals having different transfer groups.

To be more specific, the chemical compound group is a DDT compound group represented by general chemical formula 1, where X, Y, Z and L may be substituted by various functional groups.

The chemical substance to be used as the first chemical substance may be selected from a single type of substances or two types of substances, and preferably selected from two types of substances.

Next, in the electronic structure analysis section 1, the processing means sets up the initial structure of a molecule to be subjected to calculation (Step S2). Thereafter, charge is assigned to atoms constituting the molecule (Step S3). Subsequently, the processing means calculates the electronic state according to a basic equation (Step S4) and then the charge distribution is calculated (Step S5).

In Step S4, the wave function and the energy of electrons may be obtained. If the wave function is obtained, it is possible to obtain the probability of the presence of electrons (i.e., the probability distribution function) by squaring the wave function. To be more specific, the charges of individual atoms (in which the electrons are present) are obtained. When the energy of the electrons is obtained, it is possible to know the atomic arrangement (i.e., stable molecular structure) that minimizes the energy. The reason why a stable molecular structure is obtained herein is that if the molecular structure differs, the charges of individual atoms vary.

As a next step, the processing means determines whether or not the calculation of the charge distribution is completed (Step 6). If the calculation is not completed, the flow goes back to step S3 where charge is reassigned to individual atoms and step S4 to S6 are repeated.

When the calculation of the charge distribution of step 6 is completed, the processing means calculates the force applied to each of the atoms (Step S7) and determines whether the force is within a predetermined threshold value (Step 8). If the force is higher than the threshold, the processing means moves the atom in the application direction of the force (Step S9). Thereafter, the data of the resultant structure is input to Step S3 and Steps S3 to S9 are repeated until a stable structure is obtained.

Conversely, if the force applied to the atom is lower than the threshold, the processing means assigns charge to some atoms selected from the atoms constituting the chemical substance (Step 10). In Step 9, some atoms are selected according to a predetermined rule as follows. When the chemical compound has a substituent, atoms are selected except for the atoms substituted and atoms directly bound to the atoms of the substituent through a chemical bond such as a covalent bond. The charge distribution of the selected atoms may be used.

When a chemical compound group is a derivative such as DDT (dichlorodiphenyl trichloroethane) having a substituent, atoms are selected except for the whole atoms contained in the substituent and the atoms directly bound to the substituent through a chemical bond such as a covalent bond. The charge distribution of the selected atoms may be used.

The flowchart shown in FIG. 3 explains a non self-contradiction calculation method for the amount of charge. However, the calculation method is not limited to this. More specifically, potential energy may be obtained in place of the amount of charge, Furthermore, in Step S6, the forces applied to atoms are calculated to obtain a stable molecular structure. More specifically, if the forces fall within a predetermined threshold, it is determined that the calculation is completed. However, the calculation method is not limited to this. It may be determined that the calculation is completed if the moving distances of atoms become within a predetermined threshold.

Furthermore, the flowchart of FIG. 3 uses a force-field method to obtain a stable structure of a molecule. In the force-field method, the force applied to an atom is calculated and the atom is moved in the application direction of the force to obtain a stable structure. However, the method for obtaining a stable structure of a molecule is not limited to this. For example, a stable structure of a molecule can be obtained by a so-called Monte Carlo method, in which the moving direction of an atom is obtained based on a random number table.

FIG. 4 is a flowchart showing the operation procedure of the chemo-metric analysis section 3. The operation of the flowchart is performed by using the neural network shown in FIG. 5. In the neural network (shown in FIG. 5), a hidden layer is placed between an input terminal and an output terminal and connected to them. The hidden layer comprises a plurality of neurons connected in multiple layers. Such a neural network is constructed in the apparatus of the present invention under the control of the processing means in accordance with the program stored in the memory means.

Figure 5:
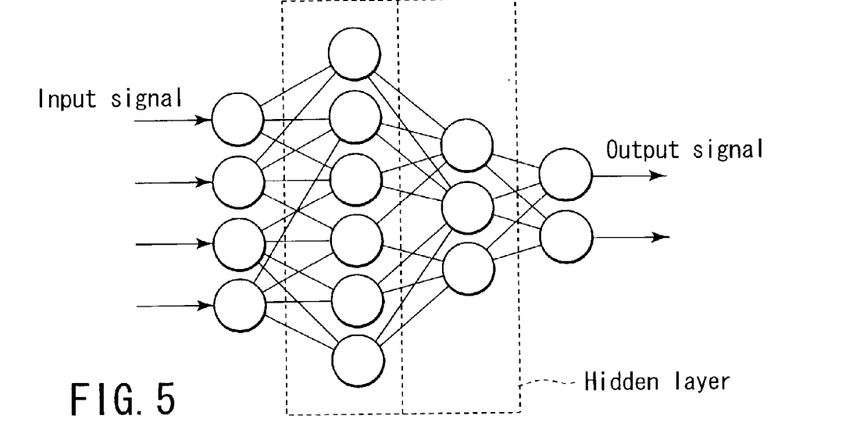
FIG. 5 shows a neural network.

In this embodiment, a case will be explained where the signal to be input to the input terminal of FIG. 5 is the charge distribution of atoms constituting a molecule of a chemical substance, whereas the signal to be output from the output terminal is a numerical value indicating the toxicity of the chemical substance.

Now, the procedure of the chemo-metric analysis section 3 will be explained with reference to the flowchart of FIG. 4. First, the processing means determines the number of input terminals of the neural network depending upon the number of input data items (corresponding to the charge distribution of individual atoms), and then, the operator (user) inputs the characteristics of the neural network, namely, network topology, from the input means (Step S11). In this case, the data output from the neural network is a toxicity index alone.

A general network topology may be employed herein. When a general network topology is used, it is preferable that a sufficiently large network having a hidden layer formed of multiple layers be set up.

After the network topology is set up, the processing means allows the neural network to learn. If no change occurs in the parameter of a neuron in the course of learning, such a neuron is, in most cases, irrelevant to the neural network. Therefore, such a neuron may be eliminated under a certain rule (which has been previously determined).

In general, when the neural network is complicated, learning with a teaching signal can be done quite well. However, the prediction accuracy tends to be low. To improve the accuracy, a forgetting rule is previously applied as one of processing procedures. When the forgetting parameter exceeds a certain value, the relevant neuron(s) may be eliminated as being irrelevant from the neural network.

Next, the processing means initializes parameters to be assigned to individual neurons within a neural network (Step 12). Random numbers may be used as initial parameters. The parameters are independently renewed so as to obtain desired results, as explained later.

Subsequently, the processing means makes the neural network learn in accordance with a learning rule (Step S13) by means of an input signal (charge distribution) and a teaching signal.

The experimentally-obtained toxicity value of a chemical substance is used as the teaching signal and the charge distribution of the chemical substance is used as the input signal. When such an input signal is supplied to the neural network, the processing means renews the parameters of neurons in such a manner that the signal output from the neural network is consistent with the teaching signal.

More specifically, the processing means determines whether the difference between the output signal and the teaching signal of the neural network falls within a permissible range (Step S14). If the difference is outside the permissible range, the processing means renews the parameters assigned to individual neurons (Step S15) and then performs the processing after Step S12.

The processing means renews the parameters assigned to individual neurons, separately or simultaneously.

Conversely, if the difference between the output signal and the teaching signal of the neural network falls within the permissible range, the processing means outputs data on the network topology and the parameters of neurons (Step S16). The output results are sent to the toxicity evaluation section 4. At this time, the processing means allows the output means to output the results.

The processing means supplies the charge distribution data of a chemical substance of unknown toxicity (second chemical substance) from the electronic structure analysis section 1 to the toxicity evaluation section 4. In the toxicity evaluation section 4, the processing means supplies the charge distribution data to the input terminals of the neural network and obtains outputs from the neural network. The outputs are the toxicity of the second chemical substance.

Figure 6:
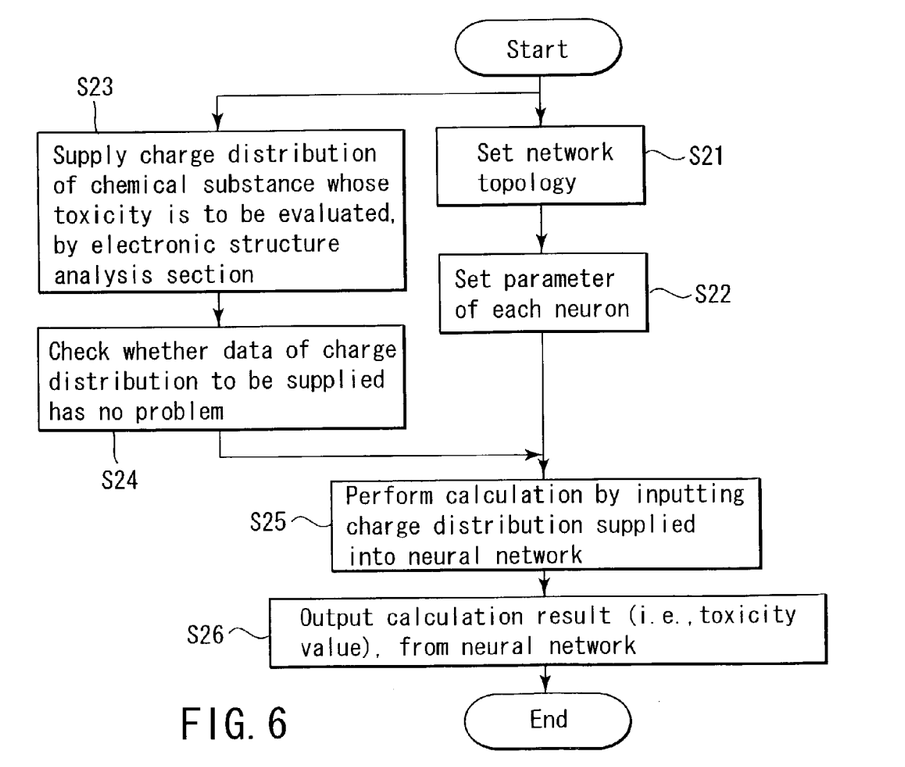
FIG. 6 is a flowchart showing the steps carried out in the toxicity evaluation section installed in the chemical substance toxicity evaluation device shown in FIG. 2.

FIG. 6 is a flowchart showing the procedure of the toxicity evaluation section 4. First, the processing means sets up a network topology based on the output from the chemometric analysis section 3 (Step S21). Thereafter, the processing means sets the weighting factors of individual neurons (Step S22). By the steps S21 and 22, the configuration of the neural network for evaluating toxicity is more specifically established.

In parallel with Steps 21 and 22, the processing means supplies the charge distribution data of the chemical substance (second chemical substance) to be evaluated for toxicity from the electronic structure analysis section 1 to the toxicity evaluation section 4 (Step S23). Subsequently, the processing means checks whether the charge distribution data supplied above have a problem (Step S24).

For example, in Step 24, the processing means determines whether the supplied data of the charge distribution falls within the range of values used in learning of the chemometric analysis section 3. If the data is outside the range, the processing means may give warning.

The case where the charge distribution of the chemical substance (second chemical substance) to be evaluated for toxicity in Step S23 is calculated in the electronic structure analysis section 1 has been explained above. However, instead of calculating the charge distribution in the electronic structure analysis section 1, the operator may input experimental data of the charge distribution to the toxicity evaluation section 4.

Next, the processing means inputs the supplied charge distribution data to the neural network, which calculates and outputs the toxicity value of the second chemical substance (Step S25). The processing means may output the toxicity value from the neural network from the output means to the operator.

As described above, the charge distribution within a molecule is used for predicting the toxicity value in the embodiment. The reason will be explained below. In order for a chemical substance such as a dioxin to function as a poison in a living body, the living body must recognize it. This involves a certain protein binding to the chemical substance and taking it into the living body. Such a protein that receives the chemical substance is sometimes called a receptor.

The binding of a chemical substance to a protein is performed roughly by the following two mechanisms.

One is a structural binding. To explain more specifically, a chemical substance binds like a key slotting into a keyhole. However, actually, such structural binding, which is considered as an ideal state of binding, rarely occurs. The other, which is more generally accepted as the mechanism, is that a chemical substance is bound to the protein by the electrical attraction between them. The latter type of binding occurs not only the case where a chemical substance is charged but also the case where a protein recognizes the intramoleuclar charge distribution of a chemical substance. Based on this, it is expected that the intramolecular charge distribution will play an important role in expressing the toxicity when substances other than dioxins are taken into the body and express their toxicities.

In this embodiment, the charge distribution of a chemical substance having an experimentally-obtained toxicity value is used as an input parameter and the toxicity value is used as a teaching signal. Further, weighting factors (parameters) are given to the individual neurons of a neural network. Using the neural network set up in this way, the toxicity value of a chemical substance of unknown toxicity is evaluated (predicted) based on the charge distribution of the chemical substance. By employing such an evaluation method in evaluating the toxicity, the accuracy of the toxicity evaluation can be improved compared to conventional methods.

The whole evaluation process needs not be performed by a single section. Instead, the evaluation process can be divided into a number of parts, that is, performed by an appropriate system. If the system process is employed, information, once obtained, can be repeatedly used, so that unnecessary expenditure may be avoided. In addition, a large-scale computer, i.e., a supercomputer (which has not been in common use) can be used in this system. A computer resource can be thus used efficiently.

Furthermore, if database and learning rules, which are desired to be originally developed, are originally developed and employed in the system (computer), the system (computer) can be easily customized. Furthermore, if the evaluation system is loaded on a PC (personal computer), any person (having no specific knowledge) can be used it as long as it is used within a correct range.

As described above, weighting factors of individual neurons of a neural network are based upon the experimentally-obtained toxicity values and the intramolecular charge distributions of certain chemical substances, and then, the toxicity values of other chemical substances are obtained by using the neural network in this embodiment. Therefore, the toxicity values of various chemical substances can be accurately evaluated in a simple manner. By using the immunotoxicity obtained in accordance with the method of Embodiment 1 as the experimentally-obtained toxicity value, the immunotoxicity of a chemical substance of unknown toxicity can be predicted.

[Third Embodiment]

In the third embodiment, the weighting factors (parameters) of individual neurons within the neural network are obtained by using database instead of carrying out the chemo-metric analysis.

Once the charge distribution is calculated with respect to a certain substance, the results can be used repeatedly. It is therefore unnecessary to calculate the charge distribution with respect to the same substance, again. Accordingly, when the toxicity values of the substances of a chemical group are evaluated in accordance with the embodiment of the present invention, the charge distributions of the substances of the chemical group are intensively calculated in a large-scale science and technology computer center having an ultra-high speed calculation machine and thereby the results can be shared.

If physicochemical data and the experimental results of various chemical substances are stored in the form of a database, the same experiment needs not to be repeated with respect to the same chemical substance. In this case, a database center may be constructed which can intensively control the physicochemical data and the experimental data of various chemical substances.

Figure 7:
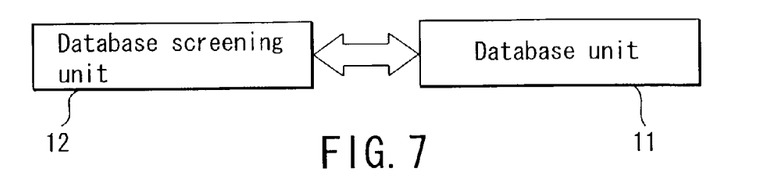
FIG. 7 shows a data flow.

To construct such a database center, a database unit 11 and a database-screening unit 12 are required as shown in FIG. 7. The database unit 11 and the data base screening unit 12 may be connected to the chemical substance toxicity evaluation apparatus mentioned above. The database screening unit 12 may comprise at least an input means, processing means, memory means and output means. These means may be integrated in the chemical substance toxicity evaluation apparatus or arranged separately from the apparatus. The database unit 11 may comprise a memory means capable of storing data and loading and unloading the data. The memory means may be formed of hardware or software.

Figure 8:
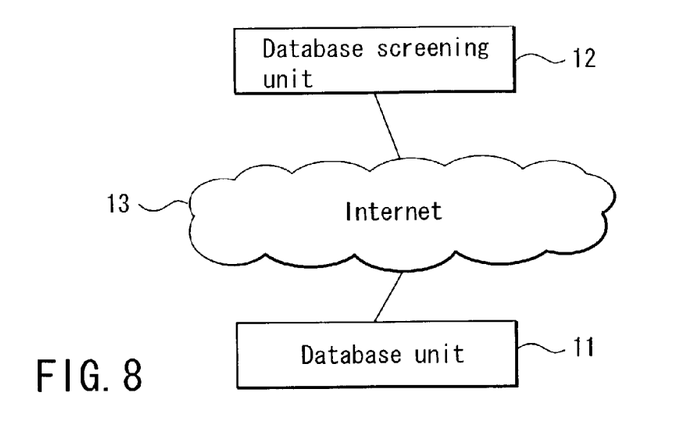
FIG. 8 shows means for getting access to a data base unit.
Figure 9:
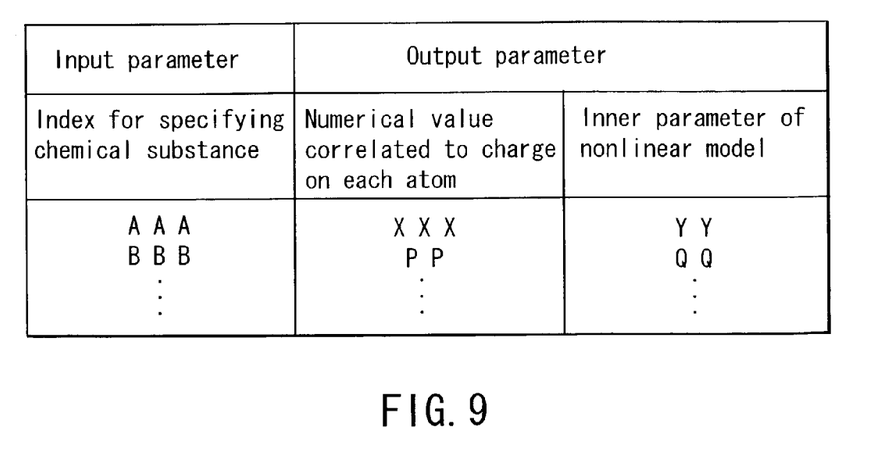
FIG. 9 is a data table to be housed.

The database screening unit 12 and the database unit 11 need not be placed next to each other. More specifically, the database screening unit 12 can get access to the database unit 11 by way of the Internet 13, as shown in FIG. 8. Alternatively, if data is stored in the database of a memory medium such as CD-ROM and DVD-ROM, a desired data can be screened by the database-screening unit 12.

In the database unit 11 shown in FIG. 7, indices capable of specifying chemical substances based on chemical formulas and chemical structures, numerical values regarding the charges of individual atoms positioned within a molecule of a chemical substance, inner parameters of a nonlinear model expressing the relationship between the experimental toxicity value of a chemical substance and the amount of charge thereof are stored in association with each other.

The "inner parameters of a nonlinear model" are the weighting factors of individual neurons of a neural network.

The database screening unit 12 shown in FIG. 7 screens the data stored in the database unit 11 based on the chemical formula and chemical structure of a chemical substance whose toxicity is to be detected. As a result, the charge of the chemical substance and weighting factors of individual neurons of a neural network are read out. Thereafter, the amount of charge read out is input into the neural network in which the weighting factors read out have been assigned to individual neurons, as an input signal, and an output is obtained. The output is the toxicity value of the chemical substance.

As described above, the values corresponding to the charges of individual atoms positioned in a chemical substance and the weighting factors of individual neurons of a neural network are read out to evaluate the toxicity of the chemical substance in the third embodiment. It is therefore unnecessary to obtain the charge distribution of the chemical substance whose toxicity is to be evaluated and to perform chemo-metric analysis. As a result, the toxicity of various chemical substances can be evaluated simply and accurately.

The chemical substance toxicity evaluation apparatus and the database unit 11 explained in the second and third embodiments may be constituted of hardware or software alone, and alternatively, constituted of hardware and software. When they are constituted of software alone, programs attaining the function of the chemical substance toxicity evaluation apparatus and data stored in the database unit 11 are stored in a recording medium such as a floppy disk or CD ROM, and allowed to read out by a computer.

The recording medium is not limited to a portable disk such as a magnetic disk or optical disk. A fixed type memory medium such as a hard disk unit or a memory may be used.

According to another aspect of the present invention, a program signal(s) may be provided for realizing an electronic structure analysis function, data input function, chemo-metric analysis function and toxicity evaluation function. By using such a program signal according to the aspect of the present invention, a chemical substance toxicity evaluation apparatus according to the aspect of the present invention may be provided.

The data within the program, which attains the function of the chemical substance toxicity evaluation apparatus and the data within database unit 11 may be distributed by way of communication lines (including wireless communication) such as the Internet 13. Furthermore, the program is encrypted, modulated, and compressed and then either distributed by means of cable communication lines or wireless communication lines, or stored in recording mediums and then distributed.

Furthermore, if the data within the database unit 11 is designed to be screened by means of the Internet 13, as shown in FIG. 8, a known robot screening system can be used. Therefore, even if a specific screening system is not newly developed, high-speed screening can be made.

In addition, if the toxicity value of the chemical substance which has been evaluated in the toxicity evaluation section 4 is added to the database unit 11, the toxicity values of various chemical substances can be obtained simply by screening the data of the database unit 11. If the amount of data stored in the database unit 11 increases, the accuracy of predicting the toxicity value of a novel chemical substance can be improved.

Now, the embodiments of the present invention will be explained in more detail by way of examples.

5. EXAMPLES

Example 1

In-vitro assay system of exogenous endocrine substance (1) Culturing of JAWS II

Dendritic cell strain JAWS II derived from the Mouse bone marrow was cultured in an α-MEM medium containing 20% fetal calf serum and 5 ng/ml of GM-CSF (granulocyte-macrophage colony stimulating factor) at 37° C. in the presence of 5% carbon dioxide.

(2) Dioxin Isomer In-vitro Assay

The cells cultured in Step (1) were recovered by trypsin treatment (0.25% trypsin). The cells thus recovered were added to a fresh α-MEM medium containing 20% fetal calf serum and 5 ng/ml of GM-CSF to prepare a cell suspension solution containing the cells in a concentration of $1 \times 10^6$ cells/mL. The cell suspension solution was dispensed by 0.7 mL into 10 sterilized Ependorf tubes. 0.7 µL of aqueous solution containing 10 mM of Brij35 in water was added to one of the 10 Ependorf tubes. To the remainder 9 tubes, Dioxin isomers (A) to (I) were respectively added. To explain more specifically, solutions each containing 100 µM of any one of the isomers in isooctane were prepared. 7 µL of each of the solutions and 0.7 µL of the aqueous solution containing 10 mM of Brij35 in water were added to the individual tubes.

The dioxin isomers used herein are as follows:

(A) 1-Chlorodibenzo-p-dioxin;
(B) 2,7-Dichlorodibenzo-p-dioxin;
(C) 1,2,4-Trichlorodibenzo-p-dioxin;
(D) 2,3,7,8-Tetraorodibenzo-p-dioxin (hereinafter, referred to as "2378-TCDD");
(E) 1,2,3,7,8-Pentachlorodibnzo-p-dioxin (hereinafter referred to as "12378-HCDD);
(F) 1,2,3,4,7,8-Hexachlorodibenzo-p-dioxin;
(G) 1,2,3,7,8,9-Hexachlorodibenzo-p-dioxin;
(H) 1,2,3,4,6,7,8-Heptachlorodibenzo-p-dioxin; and
(I) 1,2,3,4,5,6,7,8,9-Octachlorodibenzo-p-dioxin)

The Ependorf tubes were stirred by a votex mixer.

An aliquot (100 µL) was taken from each of the tubes and added to a well on a microtiter plate. The microtiter plate was cultured at 37° C. in the presence of 5% carbon dioxide. After 6 hours, 20 µL of MTS solution containing (3-(4,5-dimethylthiazole-2-il)-5-(3- carboxymethoxyphenyl)-2-(4-sulfonyl)-2H-tetrazolium, and phenazineethylsulphate was added, mixed well, and further subjected to culturing for 4 hours at 37° C. in the presence of 5% carbon dioxide. Thereafter, the absorbance of each well was measured at a wavelength of 490 nm.

(3) Determination of Toxicity

Figure 10:
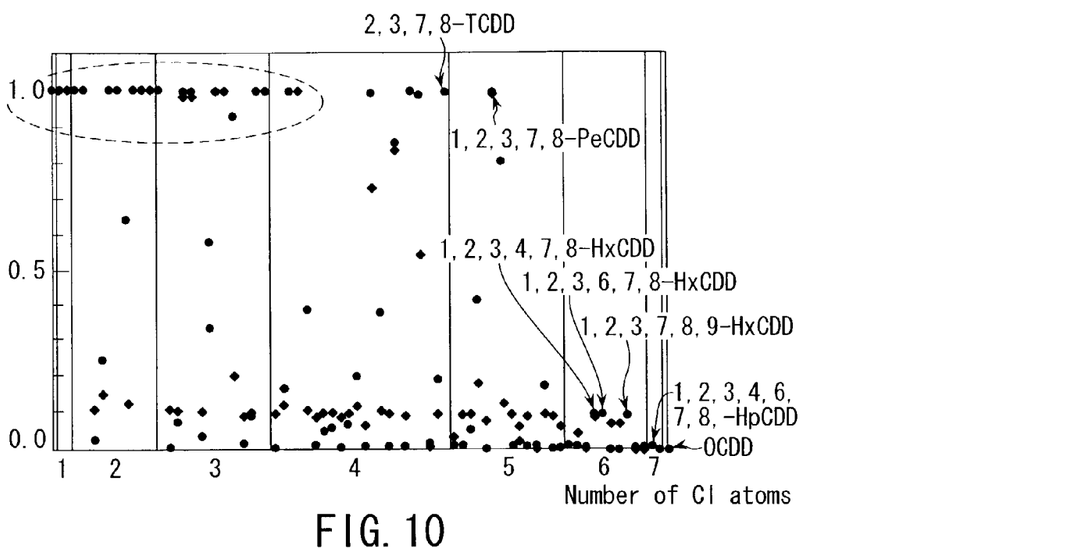
FIG. 10 is a graph showing the results of evaluating immune toxicity of several endocrine disrupting substances according to the chemical substance toxicity evaluation device presented in FIG. 2.

The absorbance values of individual wells obtained in Step (2) are compared to that of the control well (containing cells without a dioxin) to obtain absorbance ratios. FIG. 10 shows the percentage of the viabilities of the cells in the presence of test substances (A) to (I), based on the viability of the control cells (cultured in a medium containing no dioxin) being 100.

Figure 11:
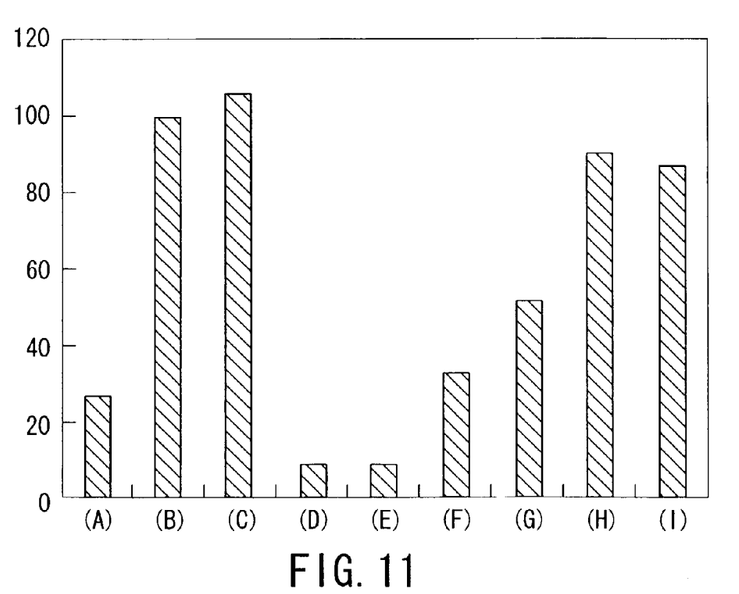
FIG. 11 is a graph showing experimental survival rate (%) of various dioxin isomers.

FIG. 11 clearly shows that there are toxic dioxin isomers other than 2378-TCDD and 12378-HCDD, which have been determined as being toxic.

As described above, according to the present invention, it is possible to evaluate the immunotoxicity of an endocrine-disrupting substance by determining the lethal effect of an endocrine disrupting substance upon immunocompetent cells. Therefore, the present invention is expected to be used in determining the toxicity of a novel substance, in future.

Example 2

Now, an example of evaluating the toxicity of a dioxin in accordance with the second embodiment of the present invention will be explained. The data obtained in Example 1 is used as experimental data. When the experimental data is used, the toxicity of a substance of unknown toxicity can be evaluated. In this example, in place of the data actually obtained in Example 1, the toxicity effective factor (hereinafter referred to as a "TEF") of a dioxin isomer published by the WHO is employed as the experimental data.

Dioxins have received particularly large public attention since they are produced undesirably (without intention). Dioxins particularly contained in the ash of small incinerators raise a serious problem. The molecular structure of a dioxin is shown in Chemical formula 2.

When the hydrogen atoms of the sites indicated by reference numerals in the chemical formula are replaced by chlorine atoms, 76 types of dioxin isomers are obtained. Among them, 2,3,7,8-TCDD has been well studied on toxicity. The toxicity value (TEF) of 2,3,7,8-TCDD is defined by the WHO (WHO 1998 TEF scheme).

Table 1 shows the toxicity level of dioxin isomers. The toxicity level is shown based on that of 2,3,7,8-TCDD being 1.

TABLE 1

| Dioxin isomer | WHO-TEF |
|---|---|
| 2,3,7,8-TCDD | 1 |
| 1,2,3,7,8-PeCDD | 1 |
| 1,2,3,4,7,8-HxCDD | 0.1 |
| 1,2,3,6,7,8-HxCDD | 0.1 |
| 1,2,3,7,8,9-HxCDD | 0.1 |
| 1,2,3,4,6,7,8-HpCDD | 0.01 |
| OCDD | 0.0001 |

When we discuss the total emission amount of dioxin isomers as an environmental problem, the toxicity levels of the dioxin isomers (TEF value) are obtained by converting them in terms of 2,3,7,8-TCDD.

The TEF value is an extremely important factor in evaluating the total emission amount of dioxins. Accordingly, on the assumption that the TEF values of 7 dioxins listed on Table 1 are data experimentally obtained, simulation (prediction) will be performed.

It is very useful that such experimental data shown in Table 1 is provided as data base shown in FIG. 7. However, the experimental data may not be provided as the database. More specifically, the operator may manually screen the data through the Internet 13, as shown in FIG. 8.

Next, the manual screening of experimental data will be explained. In this example, the case where the TEF value is used as a toxicity index according to the WHO recommendation will be explained. More specifically, a method of evaluating the toxicity of a dioxin based on the TEF value will be explained.

The molecular structures of 76 dioxin isomers are calculated in accordance with the molecular orbital method. Based on the calculation results, the charge distribution of atoms within each dioxin molecule is obtained. To handle the charge distribution easily (for the sake of convenience), charges are allocated to structural molecules in an appropriate manner, such as a Mulliken charge allocation method (Fujinaga Sigeru, "molecular orbital method", published by Iwanami Shoten, 1980, p258). As a result, it is possible to know how much charge dioxin atoms have.

As described above, the charge distribution can be obtained by numerical calculation. Alternatively, the charge distribution can be experimentally obtained. On the other hand, it is widely known that the charge distribution may be experimentally determined at atoms located at predetermined positions by use of nuclear magnetic resonance (NMR). Such a known method per se may be used.

In this manner, the charges of 22 sites within a structural molecule are calculated with respect to 76 dioxins, thereby obtaining the charge distributions thereof.

The dioxin isomers are obtained by replacing a hydrogen atom(s) present in the outermost periphery of a dioxin by a chlorine atom(S), as shown in Chemical formula 2. Since a hydrogen atom completely differs in physicochemical feature from a chlorine atom, the charge of a site greatly differs depending upon whether a hydrogen atom or a chlorine atom is placed at the site.

Furthermore, charge migration occurs between an atom of a substituting group (generally referred to as a "substituent") and an atom to which the substituent is directly bound by a covalent bond. As a result, the charge not only on the outermost peripheral portion but also on the atom covalently bonded thereto differs depending upon an isomer.

Then, in this example, the charges of atoms except substituents of an isomer and the atoms covalently bound to the substituents, in other words, the charges of six atoms represented by solid circles in Chemical formula 2 are basically used for analysis.

In this example, the correlation between the TEF values (recommended by the WHO and used as experimentally-obtained toxicity value) and the charge distribution (obtained by calculation) of 7 dioxin isomers is obtained. When the correlation is applied to an isomer of unknown toxicity (experimental data has not been obtained), the toxicity value (TEF value) can be predicted.

As a method for obtaining the correlation between numerous data items, a fitting method of a function such as the Pade approximation has been known in the statistic field. However, in this example, an approach using a neural network of a persenptoron mode is employed.

The neural network of this example has a network topology as shown in FIG. 5. A sigmoid function is applied to each neuron. To obtain desired output data from input data, the weighting factor is determined for each neuron. Since the sigmoid function is a nonlinear function, the weighting factor is determined only by repeating calculation, more specifically, a learning method called back propagation.

In this example, the charge distribution of 6 sites within a dioxin molecule is used as an input signal. As a desirable output, in other words, a teaching signal, the TEF value recommended by the WHO is used. Alternatively, each neuron is allowed to learn by the back propagation.

In the learning process, in the case where an input signal (charge distribution of a chemical substance) is given to a neural network, a process for correcting the weighting factor (parameter) of each neuron is repeatedly performed such that a teaching signal (TEF value) is output from the neural network. When the output from the neural network coincides with the teaching signal, the learning process is terminated.

Now, using the learned neural network, a TEF value of a dioxin isomer of an unknown TEF value is calculated based on the intramolecular charge distribution of the dioxin isomer.

FIG. 10 is a graphic plot of the calculation results of TEF values of dioxin isomers. The horizontal axis indicates the number of atoms and the vertical axis indicates the TEF value of dioxin isomers converted in terms of 2,3,7,8-TCDD. Plots indicated by arrows in the figure show the TEF values of dioxin isomers serving as teaching signals. Plots with no arrows show the calculation results by the neural network.

As is apparent from FIG. 10, it is elucidated that there are highly toxic dioxin isomers other than those specified by the WHO. The dioxin isomers surrounded by a dotted line in FIG. 10 are predicted to have high toxicities.

The dioxin isomers predicted to have high toxicities based on the results shown in FIG. 10 need to be subjected to a toxicity evaluation test. The method of this example may be used as a primary screening method for determining the toxicity of a chemical substance such as a dioxin isomer.

The chemical substance toxicity evaluation apparatus to be used in this example may be the same as shown in FIG. 2. Any apparatus may be used as long as it comprises an electronic structure analysis section 1, a data input section 2, a chemo-metric analysis section 3, and a toxicity evaluation section 4.

In the electronic structure analysis section 1, it is necessary to numerically solve a multidimensional integrodifferential equation according to the law of fundamental physics. To solve such an equation, it is necessary to use an analysis software well tuned up and an ultra-speed computer such as a supercomputer for running the software.

Learning can be usually performed in parallel and/or in a decentralized manner in the chemo-metric analysis section 3. The numerical calculation may be performed by a high-speed engineer workstation (EWS) or a PC cluster rather than a super computer. Such a learning may be performed at a learning center. Alternatively, if the know-how obtained in an institution is used as a learning rule, learning can be performed in the institution.

When intramolecular charge distribution data of a test chemical substance is input into the learned neural network as an input signal after learning is completed, the toxicity value of the chemical substance can be easily calculated. The computational complexity is not so high that it can be sufficiently performed by a personal computer. Specific know how is not required to perform the calculation as long as care is taken to the application range and therefore the calculation can be performed even by a non-specialist.

The results predicted in the toxicity evaluation section 4 mentioned above are used for a primary screening. Therefore, a confirmation test for the results must be performed more specifically. In this example, a confirmation test was performed by using living cells. As a result, it was demonstrated by the confirmation test that the results of the primary screening are correct based on quantitative data. The test results thus obtained may be fed back as the toxicity data of dioxins. Such a feedback path plays an extremely important role in improving a prediction accuracy.

The present invention has been described with reference to this example, which should not be construed as limiting the scope of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of evaluating the immunotoxicity of a hydrophobic test substance, comprising:
    (1) culturing JAWSII cells as immunocompetent cells in a culture system containing a hydrophobic test substance and polyoxyethylene (23) lauryl ether as surfactant, wherein the content of the polyoxyethylene (23) lauryl ether is about 30 μM or less;
    (2) obtaining a survival rate of the immunocompetent cells after the culturing (1), wherein the survival rate is obtained by a method selected from the group consisting of an MTT method, LDH method, $^3$H thymidine take-up method, and trypan blue exclusion test; and
    (3) evaluating the immunotoxicity of the hydrophobic test substance from the survival rate obtained in (2).

2. The method according to claim 1, wherein the content of the polyoxyethylene lauryl ether is in the range from about 10 μ/M to about 30 μ/M.

3. A method of evaluating the immunotoxicity of a hydrophobic test substance comprising:
    (1) culturing JAWSII cells as immunocompetent cells in a first culture system containing a hydrophobic test substance and polyoxyethylene (23) lauryl ether as surfactant and simultaneously in a second culture system containing the surfactant without the hydrophobic test substance;
    (2) obtaining a survival rate of the immunocompetent cells in each of the first and second culture systems after the culturing (1),
    wherein the survival rate is obtained by a method selected from the group consisting of an MTT method, LDH method, $^3$H thymidine take-up method, and trypan blue exclusion test; and
    (3) comparing the survival rates of the first and second culture systems obtained in (2) to each other, thereby evaluating the immunotoxicity of the hydrophobic test substance.

4. The method according to claim 3, wherein the content of the polyoxyethylene lauryl ether is in the range from about 10 μ/M to about 30 μ/M.

* * * * *